United States Patent
Oberdoerfer et al.

(10) Patent No.: US 8,714,018 B2
(45) Date of Patent: *May 6, 2014

(54) METHOD FOR THE NON-DESTRUCTIVE TESTING OF A TEST OBJECT BY WAY OF ULTRASOUND AND CORRESPONDING DEVICE

(75) Inventors: York Oberdoerfer, Cologne (DE); Wolf-Dietrich Kleinert, Bonn (DE)

(73) Assignee: GE Sensing & Inspection Technologies GmbH (DE)

( * ) Notice: Subject to any disclaimer, the term of this patent is extended or adjusted under 35 U.S.C. 154(b) by 396 days.

This patent is subject to a terminal disclaimer.

(21) Appl. No.: 12/993,429

(22) PCT Filed: Apr. 6, 2009

(86) PCT No.: PCT/EP2009/054102
§ 371 (c)(1),
(2), (4) Date: Sep. 27, 2011

(87) PCT Pub. No.: WO2009/124916
PCT Pub. Date: Oct. 15, 2009

(65) Prior Publication Data
US 2012/0024067 A1 Feb. 2, 2012

(30) Foreign Application Priority Data

| Apr. 11, 2008 | (DE) | 10 2008 018 648 |
| Apr. 18, 2008 | (DE) | 10 2008 019 778 |
| Apr. 24, 2008 | (DE) | 10 2008 001 370 |
| Jun. 16, 2008 | (DE) | 10 2008 002 450 |

(51) Int. Cl.
*G01N 29/00* (2006.01)
*G01N 29/24* (2006.01)

(52) U.S. Cl.
USPC ................................ 73/632; 73/602; 73/629

(58) Field of Classification Search
USPC ............ 73/629, 602, 622, 623, 627, 598, 632
See application file for complete search history.

(56) References Cited

U.S. PATENT DOCUMENTS 3,911,730 A * 10/1975 Niklas ............................ 73/624
4,111,557 A    9/1978 Rottenkolber et al.
(Continued)

FOREIGN PATENT DOCUMENTS

| DE | 2335567 A1 | 2/1975 |
| DE | 2901818 | 7/1980 |
| WO | 2007144271 | 12/2007 |

OTHER PUBLICATIONS

Deutsch V. et al.: "3.4 Fehlernachweis und Geratejustierung" Ultraschallpruefung: Grandlagen und Industrielle Anwendungen, XX, XX, Jan. 1, 1997, pp. 80-133, XP002280036.

(Continued)

*Primary Examiner* — Helen Kwok
(74) *Attorney, Agent, or Firm* — Cantor Colburn LLP (57) ABSTRACT

The non-destructive testing of a test object by way of ultrasound includes: (a) radiating directed ultrasonic pulses into the test object at an irradiation angle β wherein the irradiation angle β is set electronically, (b) recording echo signals that result from the ultrasonic pulses radiated into the test object, and (c) determining an irradiation position X0 in which echo signals can be recorded that can be associated with an error in the volume of the test object. The method also includes (d) determining the irradiation angle βmax for which the ERS value of the error reaches its maximum at position X0, (e) changing the irradiation position X0→X1 on the surface of the test object, the change of the irradiation position being captured, and (f) electronically adjusting the irradiation angle β in such a manner that the ERS value of the error reaches its maximum in the changed irradiation position X1.

28 Claims, 5 Drawing Sheets

(56) References Cited

U.S. PATENT DOCUMENTS

| | | | | |
|---|---|---|---|---|
| 4,305,297 | A | * | 12/1981 | Ries et al. .................. 73/628 |
| 4,682,497 | A | * | 7/1987 | Sasaki ..................... 73/602 |
| 4,744,250 | A | * | 5/1988 | Ganglbauer et al. ........... 73/588 |
| 4,866,614 | A | * | 9/1989 | Tam ...................... 600/437 |
| 5,511,425 | A | | 4/1996 | Kleinert et al. |
| 5,677,490 | A | * | 10/1997 | Gunther et al. .............. 73/622 |
| 6,382,028 | B1 | * | 5/2002 | Wooh et al. ................ 73/602 |
| 6,993,972 | B2 | | 2/2006 | Basir et al. |
| 7,204,129 | B2 | | 4/2007 | Basir et al. |
| 7,454,973 | B2 | * | 11/2008 | Baba et al. ................ 73/606 |
| 7,752,913 | B2 | * | 7/2010 | Heckel et al. .............. 73/584 |
| 7,779,694 | B2 | * | 8/2010 | Iizuka .................... 73/622 |
| 8,127,612 | B2 | | 3/2012 | Mitchell |
| 8,402,830 | B2 | * | 3/2013 | Kleinert et al. ............. 73/629 |
| 8,453,509 | B2 | * | 6/2013 | Oberdorfer et al. ........... 73/632 |
| 2006/0219013 | A1 | | 10/2006 | Baba et al. |
| 2006/0241456 | A1 | | 10/2006 | Karasawa |
| 2009/0320601 | A1 | * | 12/2009 | Kleinert .................. 73/628 |
| 2011/0016978 | A1 | | 1/2011 | Kleinert et al. |
| 2011/0016979 | A1 | | 1/2011 | Oberdorfer et al. |
| 2012/0024067 | A1 | | 2/2012 | Oberdoerfer et al. |
| 2012/0095346 | A1 | | 4/2012 | Yoshizawa et al. |
| 2012/0099397 | A1 | | 4/2012 | Inoue et al. |

OTHER PUBLICATIONS

International Search Report; PCT/EP2009/054102; Oct. 5, 2009.

International Search Report, PCT/EP2008/067044, Dated Mar. 20, 2009, European Patent Office.

International Search Report; International Application No. PCT/EP2008/068236; dated May 25, 2009.

Bohn H, et al. "Apparative Development for in-service Inspections of reacotr pressure vessels" Nuclear Engineering and Design, Amsterdan, NL, vol. 102, No. 3, Jan. 1, 1987, pp. 341-355, XP002448121, ISSN: 0029-5493.

Deutsch V, et al. "3.4 Fehlernachweis und Geratejustierung" Ultraschallpreufung: Grundlagen Und Industrielle Anwendungen, Jan. 1, 1997, pp. 80-145, XP002301049.

Grohs B, et al. "Characterization of Flaw Location, Shape, and Dimensions with the Alok System" Materials Evaluation, Columbus, OH, US, vol. 40, No. 1, Jan. 1, 1982, pp. 84-89, XP009030157 ISSN:0025-5327.

Olympus, "Olympus NDT Introduces a Manual Weld Inspection Solution That Includes conventional UT and Phased Array", http://www.ndt.net/search, Waltham MA, Apr. 23, 2008, NDT.net Issue: May 2008, p. 1.

Olympus, "Phased Array Probe Update" Weld Probe Series (WPS), Innovation in NDT, 920-143A-EN, www.olympusNDT.com, PA_Probe_Update_WPS_EN_0804, Canada, 2006, pp. 1-2.

Olympus, "Phased Array Probe Update" AWS and DGS Probes, Innovation in NDT 920-144A-EN, www.olympusNDT.com, PA_Probe_Update_DGS-AWS_EN_0804, Canada, 2006 Olympus NDT, pp. 1-2.

Olympus, "Ultrasound, UT Phased Array, Eddy Current, and EC Array" OmniScan MX, Innovation in NDT 920-061E, OmniScan_MX_EN_0611, Canada, 2003-2006 Olympus NDT, www.olympusNDT.com, pp. 1-14.

Olympus, "Entry-Level Manual Phased Array Solutions", OmniScan M, Innovation in NDT 930-168, www.olympusNDT.com, OmniScanM_EN_0712, Canada, 2006 Olympus NDT, pp. 1-2.

Olympus, "Phased Array Ultrasound Probe Catalog" Innovation in NDT, www.olympustNDT.com, Fourth Edition, Nov. 2006, PA_Probe_Catalog_EN_0611, Canada, 2003-2006 Olympus NDT, pp. 1-24.

Olympus, "Manual Weld Inspection Solution" Convential and Phased Array UT, Innovation in NDT 920-135A-EN, www.olympusNDT.com, OmniScan_Manual_Weld_EN_0804, Canada, 2008 Olymput NDT, pp. 1-3.

RD Tech, "Phased-Array Ultrasound Probe Catalog 2005-2006", Third edition, May 2005, PA_Probe_Catalog_9505, Canada, 2004-2005 R/D Tech Inc., www.rd-tech.com, pp. 1-24.

Olympus, "New Bei Olympus NDT: Ultraschallbilder Mittels Phased Array—Die Neuen Ultraschallprufgerate der EPOCH 1000 Serie", http://www.olympus.at/corporate/1696_3065.htm, Jan. 1, 2009, Hamburg, Jan. 2009, pp. 1-3.

RD Tech, "Ultrasound Phased-Array Transducer Catalog 2004-2005", R/D Tech Ultrasonic Transducers, Canada, 2004 by R/D Tech Inc., pp. 1-11.

RD Tech, "Innovation in NDT" Nondestructive Testing, Panametrics-NDT, A business of D/D Tech Instrumnets Inc., NDT engineering corporation, R/D Tech Inc. Aug. 2004, pp. 1-15.

RD Tech, "Ultrasound Phased—Array Probe Catalog 2003-2004" www.rd-tech.com, First edition, Nov. 2003, PA_Probe_Catalog 1103, Canada, 2003, R/D Tech Inc., pp. 1-18.

* cited by examiner

METHOD FOR THE NON-DESTRUCTIVE TESTING OF A TEST OBJECT BY WAY OF ULTRASOUND AND CORRESPONDING DEVICE

FIELD OF THE INVENTION

The subject matter of the present invention is a method for nondestructive testing of a test object by means of ultrasound, whereby within the context of the method, an equivalent reflector size is determined for a flaw in the volume of the test object by using ultrasonic echo signals that are recorded within the context of the method. Further, the subject matter of the present invention is a device that is suitable for carrying out the method according to the invention.

BACKGROUND OF THE INVENTION

Generic methods are well known in prior art. A flaw detected in the volume of the test object by means of an pulse echo method based on insonifying pulsed ultrasound into the test object, for example, a cavity, an inclusion or also a crack, are characterized by specifying a value for its equivalent reflector size ERS. The value of this equivalent reflector size is determined by a comparison of the amplitudes of the echo signals that are caused by the tested flaw in the volume of the test object, with the model of a comparative flaw of known size. In the so-called reference body method, the test operator compares the echo signals of the tested test object with the echo signals which he obtains on a reference body that is equivalent to the test object, which has one or more reference reflectors. For example, for this purpose, cylindrical bores with known dimensions can be inserted into the reference body. The echo signals occurring at the bore during an ultrasound reflection are then compared with echo signals that are obtained while testing the test object. In the reference body method, the test operator therefore uses a suitable test probe, that can be, for example, a suitable angle test probe, to take measurements both of the test object that is to be tested, as well as of the prepared reference standard.

In contrast, in the so-called DGS method, the amplitude of an echo signal resulting from a flaw in the volume of the test object is compared with a theoretically calculated and/or empirically determined echo signal of a model reference flaw, which is assumed to be a plane circular disk, as a rule, and which is at the same depth in the test object as the flaw detected during the test of the test object. For this purpose, a so-called DGS diagram is prepared in advance for the test probe used in the test, which contains the characteristics of the test probe. The curves contained in the DGS diagram indicate the echo amplitude that would be produced by a reference flaw in a measurement with the test probe that is used. In a practical testing task, the test operator can then read the equivalent reflector size of the flaw detected in the volume of the test object by carrying out a sound-attenuation correction (material-specific sound attenuation) and transfer correction (test object-specific coupling losses) for the test object directly off the DGS diagram.

In a classic test method according to the DGS method, the test operator varies the test probe position and orientation relative to the flaw found and tries to thereby maximize the resulting echo signal. This process is also described as "breeding" the ultrasound signal when testing materials by means of ultrasound. The actual determination of the equivalent reflector size of the detected flaw then takes place for the maximized ultrasound echo.

Additional details of the DGS method result, for example, from patent specification U.S. Pat. No. 5,511,425 A, which goes back to the legal predecessor of the applicant. Furthermore, the DGS method is described in detail in the book "Material Testing with Ultrasound", J. Krautkrämer and H. Krautkrämer, 5th edition, Springer Verlag, ISBN 3-540-15754-9, chapter 19.1, pages 343-349. The technical details concerning the DGS method disclosed here are being added in their entirety to the content of the disclosure of this application by way of this reference.

In its currently prevalent form, it is a disadvantage of the DGS method that, for a meaningful characterization of a flaw in the volume of a test object, a test must be performed with a plurality of test probes. This is due to the fact that, for a given flaw, a perpendicular insonification into the test object does not necessarily supply a maximum echo amplitude. Rather, it depends on the orientation of the flaw in the volume of the test object under which insonification angle a maximum echo signal can be obtained. In order to actually obtain a value for the equivalent reflector size of a detected flaw that is reasonably correlated with the actual size of the flaw, therefore, as a rule, different angle test probes are used within the context of standardized test procedures based on the DGS method, which realize different insonification angles. In practice, this method signifies a considerable testing and documentation effort for the test operator, so that as a rule, testing is only performed under a few insonification angles. Moreover, the variation of the insonification angle requires a change of the test probe, which causes additional problems because of the calibration, which is never absolutely unequivocal, and the coupling properties of the test probes. This also renders the interpretation of the ERS values found on a flaw more difficult.

SUMMARY OF THE INVENTION

Therefore, it is the object of the present invention to propose a method for nondestructive testing of a test object by means of ultrasound by means of which the test operator can obtain test results in a simple manner, from which a novel representation of a flaw found in the volume of the test object. Further, a device is to be provided that is suitable for carrying out the method according to the invention.

This object is accomplished by a method having the features of claim 1 and a device having the features of claim 16.

A method according to the invention is provided for the nondestructive testing of a test object by means of ultrasound. In particular, it is provided for creating a novel graphic representation of a flaw found in the volume of a test object. The method according to the invention comprises the following process steps:

a. Insonification of directed ultrasonic pulses into the test object at an insonification angle $\beta$, wherein the insonification angle $\beta$ is adjusted electronically, b. Recording of echo signals that result from the ultrasonic pulses insonified into the test object, c. Determining an insonification position X0 at which echo signals can be recorded which can be allocated to a flaw (102) in the volume of the test object, d. Determining an insonification angle $\beta$max for which the ERS value of the flaw becomes has its maximum at the position X0, e. Changing the insonification position X0→X1 on the surface of the test object, wherein the change of the insonification position is detected, and f. Electronic tracing of the insonification angle $\beta$, such that the ERS value of the flaw (102) at the changed insonification position X1 has its maximum.

The insonification angle can be traced electronically, for example, by determining, based on the position X0 determined in partial step d and the associated insonification angle $\beta$max and the detected change of the insonification position from X0 to X1 on the surface of the test object and the depth of the flaw in the test object, by means of simple geometric considerations the angle $\beta$ for which the ultrasonic pulses insonified into the test object coincide at the same position at the depth of the flaw in the test object. The depth of the flaw in the test object can in this case be determined simply, for example, from the echo delay time and the insonification angle $\beta$.

In an alternative approach, the above-described active tracing of the insonification angle $\beta$ is dispensed with; rather, in the context of the method according to the invention, the insonification angle $\beta$max (X1) for the changed insonification position X1 is determined again, when the change of the insonification position on the surface of the test object, for which the ERS value of the flaw has its maximum at the position X1.

In a preferred embodiment of the method according to the invention, a graphic representation of the maximum ERS value of a flaw found in the volume of the test object is generated within the context of the method as a function of the insonification angle $\beta$. Such a graphic representation can be generated in a very simple manner by means of the above-described method, because the angle $\beta$max (X) for which the ERS value has its maximum is directly determined within the context of the method when the insonification position X is changed. Consequently, for a direction of movement of the ultrasonic transmitter on the surface of the test object, the ERS value of the flaw is obtained for which the ERS value of the flaw has its maximum at the given insonification position X, dependent on the insonification position X or correlated directly therewith as a function of the insonification angle $\beta$max (X). It is immediately clear that corresponding graphic representations of the flaw can be produced from different spatial directions by the ultrasonic transmitter being guided in just that spatial direction on the surface of the test object. It is thus possible to generate a two-dimensional image of the flaw found in the volume of the test object.

It was found within the context of complex experiments that the ERS value of a flaw often is strongly dependent upon the angle under which the flaw is insonified. This angle is directly correlated with the insonification angle $\beta$ under which angle the ultrasound insonified according to the method into the test object is coupled into it. It has been proven thereby that the observed angular dependence of the ERS value of a flaw allows conclusions to be drawn about essential properties of a flaw, such as, for example, the geometry thereof such as flat or voluminous, in particular the symmetry thereof.

In particular it has been found that a classification of a flaw found in the volume of a test object can be made based on the angular dependence of its ERS signal. Accordingly, it is much easier for the tester if he has at his disposal a graphic representation of a flaw that he has detected in the volume of the test object, from which he can draw conclusions at least qualitatively as to the dependence of the ERS value of the flaw on the ensonification angle or insonification angle $\beta$.

In an advantageous further development of the method according to the invention, a B scan, C scan or sector scan of the test object is generated within the context of the method. In the process, at least one ERS value of a flaw found in the volume of the test object is depicted in the generated scans. Preferably, this is the maximum ERS value of the flaw detected during a variation of the insonification angle $\beta$ while insonifying the flaw in a predetermined spatial direction. Preferably, the insonification angle $\beta$ at which the ERS value of the detected flaw is at maximum is shown in the generated scan, e.g., by representing the ERS value of the flaw as a bar whose size is correlated to the ERS value of the flaw and whose orientation is perpendicular to the direction, at which the maximum ERS value of the flaw is produced.

In a further preferred embodiment of the method according to the invention, the influence of the electronic adjustment of the insonification angle $\beta$ on the detected ERS value of the flaw is automatically compensated (by calculation). This can be carried out particularly easily if a transmitting test probe is used for insonification of the directed ultrasonic pulses whose ultrasonic transmitter comprises a plurality of independently controllable ultrasonic transducers. In order to electronically adjust the insonification angle $\beta$, the plurality of ultrasonic transducers are then controlled individually and phase-accurately in such a way that the emission angle $\alpha$ of the ultrasound transmitter, and thus the insonification angle $\beta$, is varied.

Preferably, a transmitting test probe is used for insonification of the directed ultrasonic pulses into the test object, whose ultrasonic transmitter comprises a plurality of independently controllable ultrasonic transducers. For the adjustment of the insonification angle $\beta$, the plurality of ultrasonic transducers is then controlled individually and phase-accurately in such a way that the emission angle $\alpha$ of the ultrasound transmitter is varied. This directly results in a variation of the insonification angle $\beta$ in the test object.

Preferably, it is provided in the context of the method according to the invention that, when the ERS value of the flaw detected in the volume of the test object is calculated from the echo signals that can be allocated to the flaw, the influence of the electronic adjustment of the emission angle $\alpha$, and thus of the insonification angle $\beta$, on the detected ERS value of the flaw is automatically compensated by calculation. The angle of emission and insonification angle are to be considered equivalent within the context of the present invention, since they are firmly linked to one another physically. In particular this means that in the context of the method according to the invention at least one, but preferably several, of the following corrections is carried out automatically:

Compensation of the change of the virtual ultrasonic transducer size or the aperture associated therewith of the ultrasonic transducer during the change of emission angle $\alpha$ or insonification angle $\beta$, Compensation of the change of the position of the coupling-in point of the ultrasound emitted by the ultrasonic transducer into the test object during the change of emission angle $\alpha$ or insonification angle $\beta$, and Compensation of the change of position of the focus in the test object during the change of emission angle $\alpha$ or insonification angle $\beta$, Compensation of the change of the sound path in the leading body resulting from the change of emission angle $\alpha$.

The phased array test probes already mentioned have particular advantages for the electronic adjustment of the insonification angle $\beta$. However, this does not mean that other ultrasonic test probes with variable insonification angle could not be used within the context of the method according to the invention, provided that that the insonification angle is electronically adjustable and also quantifiable.

Within the context of the method according to the invention, advantageously at least one DGS diagram is used to determine the ERS value of a flaw in the volume of the test object from the echo signals reflected by the flaw. In the process, this DGS diagram can be specific to the source of the ultrasonic pulses, that is, in particular specific for the transmitting test probe used. Furthermore, the DGS diagram can be specific for the material of the test object. In a first embodiment, the DGS diagram furthermore exhibits a dependence on the insonification angle β of the ultrasound into the test object or an equivalent angle size. In an alternative approach, the DGS diagram does not show any dependence on the insonification angle β, instead the influence of the insonification angle β on the registered echo amplitude or the ERS value of the flaw is compensated by calculation within the context of the method.

Furthermore, within the context of testing the test object preferably at least one calibration step is carried out. In this step, the amplitude of an echo caused by a reference flaw is detected. The reference flaw is preferably a back face or a test bore of a test body, wherein in particular in the case of the back face echo a separate test piece can also be dispensed with and the calibration step can be carried out directly on the test object itself. Preferably, the calibration step is carried out for a plurality of insonification angles and/or reference flaws, but this is not mandatory.

The device suitable for carrying out the method according to the invention, which will be described in more detail below, in this case preferably offers the possibility of carrying out standardized calibrations steps, in which, e.g., a selection can also be made among a plurality of preadjusted standardized test pieces.

In a preferred embodiment of the method, at least one of the following characteristics of the flaw is shown in the graphic representation generated:
  a) The insonification angle β at which the ERS value of the flaw is at maximum,
  b) Information on whether the ERS value of the flaw is substantially constant over different insonification angles β, or whether it varies at different insonification angles.

In particular a detected flaw can be symbolized by a bar in the generated B-scan, the extension of which along its longitudinal axis correlates with the ERS value of the detected flaw. Advantageously, the same scales are used in the process for the representation of the ERS value and for the X position on the surface of the test object. In the context of the present invention, any geometric figure is to be considered a bar which is a mirror-symmetrical with respect to two axes that are orthogonal with respect to each other, for example, a line, a rectangle, an ellipsis, etc. In connection with the present invention, one of the two symmetry axes of the bar is in this case referred to as its longitudinal axis.

In order to increase the interpretability of the B-scan generated within the context of the method according to the invention, in particular to improve the intuitive comprehensibility of the generated B-scan, it has proven to be advantageous if at least one of the following further characteristics of the detected flaw is shown in the generated B-scan in a suitable manner:
  a) The relative amplitude of the flaw echo,
  b) The insonification angle β at which the ERS value of the detected flaw is at maximum, e.g., by the flaw is shown as a bar, perpendicular to the insonification direction at which the ERS value of the flaw is at maximum,
  c) The relative flaw size,
  d) Information on the sound path of the echo, e.g., the leg, from which the flaw echo originates, and
  e) Information on whether the ERS value of the detected flaw is the same or different over all of the checked insonification angles β within the range of predetermined flaw limits.

The specification of relative values can relate, e.g., to reference values measured in connection with the testing of the test object.

One or more of the following display parameters can be advantageously used in the B-scan for this purpose:
  a) The color of the bar,
  b) The dimension of the bar transverse to its longitudinal axis (bar width B),
  c) The angle of the longitudinal axis of the bar relative to the surface of the test object, and
  d) The geometric basic form of the bar.

Several representation options for different flaw characteristics are now explained by way of example in more detail below.

Within the context of the present invention, relative amplitude of the flaw echo is to be understood as the information on whether the ultrasonic echo originating from the flaw in the volume of the test object, i.e. the amplitude of the echo, exceeds a certain predetermined threshold. A threshold of this type can relate, for example, to the measured flaw echo amplitude compared to the amplitude of a reference flaw. In particular, a threshold can be given in "ERS millimeters," e.g., the ERS should be greater than or equal to a registration limit of, for example, 2 millimeters or 5 millimeters.

If within the context of the method according to the invention the insonification angle β is varied and the insonification angle β determined at which the ERS value of the flaw is at maximum, the tester can be given an indication of the orientation of the flaw in the volume of the test object, by the longitudinal axis of the bar representing the flaw in the B-scan is shown tilted with respect to the surface of the test object. Advantageously, the bar is shown in this case such that its longitudinal axis stands perpendicular on the acoustic axis of the ultrasound insonified at the angle α for which the ERS value of the flaw is at maximum.

Another information that is relevant for the tester and the documentation is whether the ERS value of the detected flaw is above or below a predetermined registration limit. It is thus possible, for example, to completely suppress flaw signals below a specific threshold in the generated B-scan. Alternatively, flaw signals of this type can also be color-coded or shown as transparent bars in order to show the distance from the registration limit (e.g. in "ERS mm" or dB). In particular the last two representation options provide the advantage that it can be indicated to the tester that, although a flaw is present in the volume of the test object at the tested location, it is so small in terms of its ERS value that it does not have to be documented based on the applicable test specifications.

Furthermore, it can be of interest for the tester to know from which sound path, that is, e.g., "leg" of the insonified ultrasonic beam, the flaw echo results. This information is of interest in particular when a test is being carried out on a test object with plane-parallel surfaces, since in this case the situation often occurs that the flaw is not detected by the ultrasonic beam until it has been reflected at least once on the back face of the test object. This information can be determined from the propagation time of the flaw echo and shown in the B-scan as a graphic representation for the tester, for example, by color-coding the bar.

Furthermore, the information is of interest to the tester on whether the detected flaw in the volume of the test object rather extends in a flat manner or is to be considered a three-dimensionally extended flaw. The three-dimensionally extended flaws are generally voids or defects that are due to manufacturing and often do not pose a risk of fatigue fractures. In contrast, extended planar flaws are generally correlated with cracks in the test object, which can be signs of fatigue and have a marked tendency to spread, which can lead to fatigue fractures. A three-dimensionally extended flaw in the volume of the test object is characterized in the context of the method according to the invention in that the resulting ERS value of the flaw is substantially independent of the insonification angle. In contrast, two-dimensionally extended flaws show a marked dependence on the insonification angle. Therefore, the information on whether it is a planar extended flaw or a three-dimensional flaw can in this case be coded in the bar shown. This can take place, for example, by adjustment of the length and width of the bar shown or also by the selection of a geometric form that represents the symmetry of the flaw. However, a color-coding can also be used at this point advantageously.

Alternatively to the generation of a B-scan described in detail above, the generation of a C-scan (X-axis: Position in the x direction on the surface of the test object, Y-axis: Position in the Y direction on the surface of the test object) or the generation of a sector scan (also S-scan, X-axis: distance from the insonification location/depth in the test object, Y-axis: azimuth angle: insonification angle) can be provided and can be advantageous in special cases. All of the above statements on the representation of the determined flaw characteristics in the B-scan can also be applied directly to the furthermore provided C-scans and S-scans.

The method according to the invention permits carrying out the DGS method prescribed in many test specifications with modern ultrasonic test probes that permit an electronic adjustment of the insonification angle into the test object, for example, using the phased array technique.

A method according to the invention is provided for the nondestructive testing of a test object by means of ultrasound. A device of this type comprises a transmitting test probe with an ultrasonic transmitter, which is configured to insonify directed ultrasonic pulses at an insonification angle $\beta$ into the test object. Furthermore, the device comprises an ultrasonic receiver, which is configured to record echo signals of the ultrasonic pulses insonified into the test object. A control and evaluation unit furthermore provided is configured to control the ultrasonic transmitter of the transmitting test probe such that the ultrasonic transmitter is excited to emit ultrasonic pulses. Furthermore, the control and evaluation unit is configured to process the echo signals recorded by the ultrasonic receiver and to determine an ERS value of the flaw from echo signals that can be assigned to a flaw in the volume of the test object.

According to the invention the ultrasonic transmitter of the device now has a plurality of ultrasonic transducers that can be controlled independently. Furthermore, the control and evaluation unit is configured to control these ultrasonic transducers individually exactly in phase such that the emission angle $\alpha$ of the ultrasonic transmitter and thus the insonification angle $\beta$ into the test object can be adjusted electronically. Furthermore, the control and evaluation unit is configured to determine the ERS value of a flaw in the volume of the test object for a plurality of insonification angles from echo signals that can be assigned to the flaw.

Finally, the control and evaluation unit is configured to determine an insonification position $X0$ at which echo signals that can be assigned to a flaw in the volume of the test object can be recorded, and to determine the insonification angle $\beta max$ for which the ERS value of the flaw has its maximum at the position $X0$. It is furthermore configured, in the case of a change of the insonification position $X0 \rightarrow X1$ on the surface of the test object, to detect the change of the insonification position and the electronically trace the insonification angle $\beta$ such that the ERS value of the flaw at the changed insonification position $X1$ has its maximum.

In a simplified embodiment of the method according to the invention, in the case of a change of the insonification position $X0$-$X1$ on the surface of the test object, the change of the insonification position is detected and the insonification angle $\beta$ electronically traced such that the sound beam strikes the flaw always at the same position. A maximization of the ERS value by means of an additional angle variation is in that case dispensed with.

In preferred further developments, the control and evaluation unit is designed to carry out the method according to the invention in its various forms and developments.

In a particularly preferred embodiment, the control and evaluation unit is configured in particular to generate a graphic representation of the flaw mentioned above from which the dependence of the determined ERS value of the flaw on the insonification angle $\beta$ can be read off at least qualitatively.

In particular the generated graphic representation can reflect the ERS value of the flaw in direct dependence on the insonification angle $\beta$. From the angular dependence of the ERS value of the flaw, the tester, as was already discussed in detail above, can draw conclusions as to essential properties of the flaw. In an alternative approach, the generated graphic representation of the flaw is a B-scan, a C-scan or a sector scan of the test object, in which the angle-dependent ERS value of the flaw is recorded in a suitable manner.

In a particularly preferred embodiment of the device according to the invention, which is advantageous in particular in connection with the generation of a B-scan, C-scan or sector scan of the test object, the device further comprises a path detection unit, which is configured to detect a change in the position of the test probe on the surface of the test object. Such a path detection unit can be realized, for example, by means of a mechanical displacement sensor arranged on the test probe itself. However, displacement sensors that work optically according to the principle of the optical mouse can also be used. Finally, when a phased-array ultrasonic transmitter is used, the changes of the ultrasonic signals that occur during a position change of the test probe on the surface of the test object can also be utilized for determining a position. Reference has already been made to the corresponding passages in the literature. The use of a linear array, in addition to the detection of a change in position of the test probe on the surface of the test object in the direction of the longitudinal axis of the array, permits carrying out an electronic scan in this direction, by different subgroups of transducers being activated successively. The use of a two-dimensional phased array permits in particular the detection of a position change in two directions in space, and furthermore the detection of a rotation of the test probe on the surface of the test object.

The possibilities of depicting essential flaw properties in the graphic representations of the flaw generated have already been dealt with in detail in connection with the method according to the invention. The device according to the invention is preferably configured to generate the representations of the flaw explained in connection with the method.

Finally, particular advantages result when the control and evaluation unit is configured to automatically compensate for the influence of the electronic adjustment of the insonification angle on the ERS value of the flaw to be determined in the calculation of the ERS value of the flaw.

As has already been explained in connection with the method according to the invention, the ERS value of a flaw can be automatically determined, for example, by comparison with a plurality of stored reference values, wherein these reference values can be, for example, one or more DGS diagrams. In this context it is pointed out that, in order to determine an ERS value of a detected flaw by means of the method according to the invention, a reference echo, e.g., from a test object must be available, in addition to a DGS diagram, for each angle at which the flaw is ensonified.

In a particularly preferred embodiment, a plurality of reference values are stored in the control and evaluation unit, for example, in the form of DGS diagrams, which are correlated in groups with different insonification angles $\beta$. In this case, these reference values can furthermore be test probe-specific. In particular, this can therefore be a test probe-specific quantity of DGS diagrams for various insonification angles $\beta$. Preferably, the test probe is furthermore provided with an electronic identifier that makes it possible for the control unit, when the test probe is connected, to recognize automatically the test probe type or even the individual test probe and to select the stored test probe-(type) specific reference values.

In all of the embodiments, however, the determination of an (insonification angle-specific) ERS value for a detected flaw generally presupposes that a reference value is available, which, e.g., was detected on a test piece at the respective angle or originates from an interpolation between different measured angles.

Particular advantages result when the control and evaluation unit is configured, in the calculation of the ERS value of the flaw, to automatically compensate for the influence of the electronic adjustment of the insonification angle $\beta$ on the ERS value of the flaw to be determined.

Thus, in a particularly preferred embodiment of the device according to the invention, the control and evaluation unit thereof is configured to automatically calculate, from the angle of emission $\alpha$ of the ultrasonic transmitter, the insonification angle $\beta$ resulting in the test object, in order to automatically compensate for the influence of the electronic adjustment of the insonification angle $\beta$ on the ERS value of the flaw to be determined. In particular, this compensation can be designed to be test probe-specific. Furthermore, it will be practically configured to take into consideration the ultrasound-specific properties of the material of the test object such as, for example, the sonic speed.

A further improvement can be achieved when, for the automatic compensation for the influence of the electronic adjustment of the insonification angle $\beta$ on the ERS value of the flaw to be determined, the control and evaluation unit of the device according to the invention is configured to automatically compensate for the variation of the virtual ultrasonic transmitter size associated with the electronic variation of the insonification angle $\beta$ and thus the aperture of the test probe. The virtual ultrasonic transmitter size results from a projection of the actual geometric dimension of the ultrasonic transmitter onto one perpendicular to the electronically adjusted emission direction of the ultrasonic transmitter. If the ultrasonic transmitter emits at an emission angle $\alpha$ differing from 0°, this results directly in a reduction of the virtual ultrasonic transmitter size. Since the ultrasonic transmitter size may be included in the calculation of the ERS value of a detected flaw, a corresponding automatic compensation possibly has to take place in this case.

A further improvement results when the control and evaluation unit is configured to automatically compensate for the influence of the displacement of the coupling-in location X0, which is associated with an adjustment of the emission angle $\alpha$ or of the insonification angle $\beta$, on the ERS value of the flaw to be determined. The change of the sound path length in the leading body during a change of the emission angle $\alpha$ can also be compensated for automatically in this case.

Finally, an automatic compensation can also be provided for the position change of the focus in the test object, which results during a variation of the emission angle $\alpha$ due to the change of the sound path length in the leading body resulting therefrom.

In conclusion, it should be pointed out that the automatic compensation according to the invention for the influence of the electronic adjustment of the insonification angle $\beta$ on the ERS of the flaw to be determined on the basis of stored DGS diagrams can be carried out in two different ways. On the one hand, the control and evaluation unit can be configured to normalize the actual measured values (i.e., time-resolved echo signals) taking into account the influence of the adjustment of the insonification angle $\beta$, i.e., for example, to convert to the results of a conventional test probe with fixed insonification angle $\beta$. These are then compared to a standardized DGS diagram.

On the other hand, the test probe-specific influences of the electronic angle adjustment on the echo signals can already be taken into account during the production of the DGS diagrams stored in the control and evaluation unit; i.e., the compensation to be carried out is already taken into account in the stored DGS diagrams. This implementation is also supposed to be covered by the method according to the invention and the device according to the invention.

Further advantages and features of the device according to the invention and the method according to the invention result from the dependent claims and the exemplary embodiments, which are explained in more detail below with reference to the drawing.

DETAILED DESCRIPTION OF THE DRAWINGS

Figure 1:
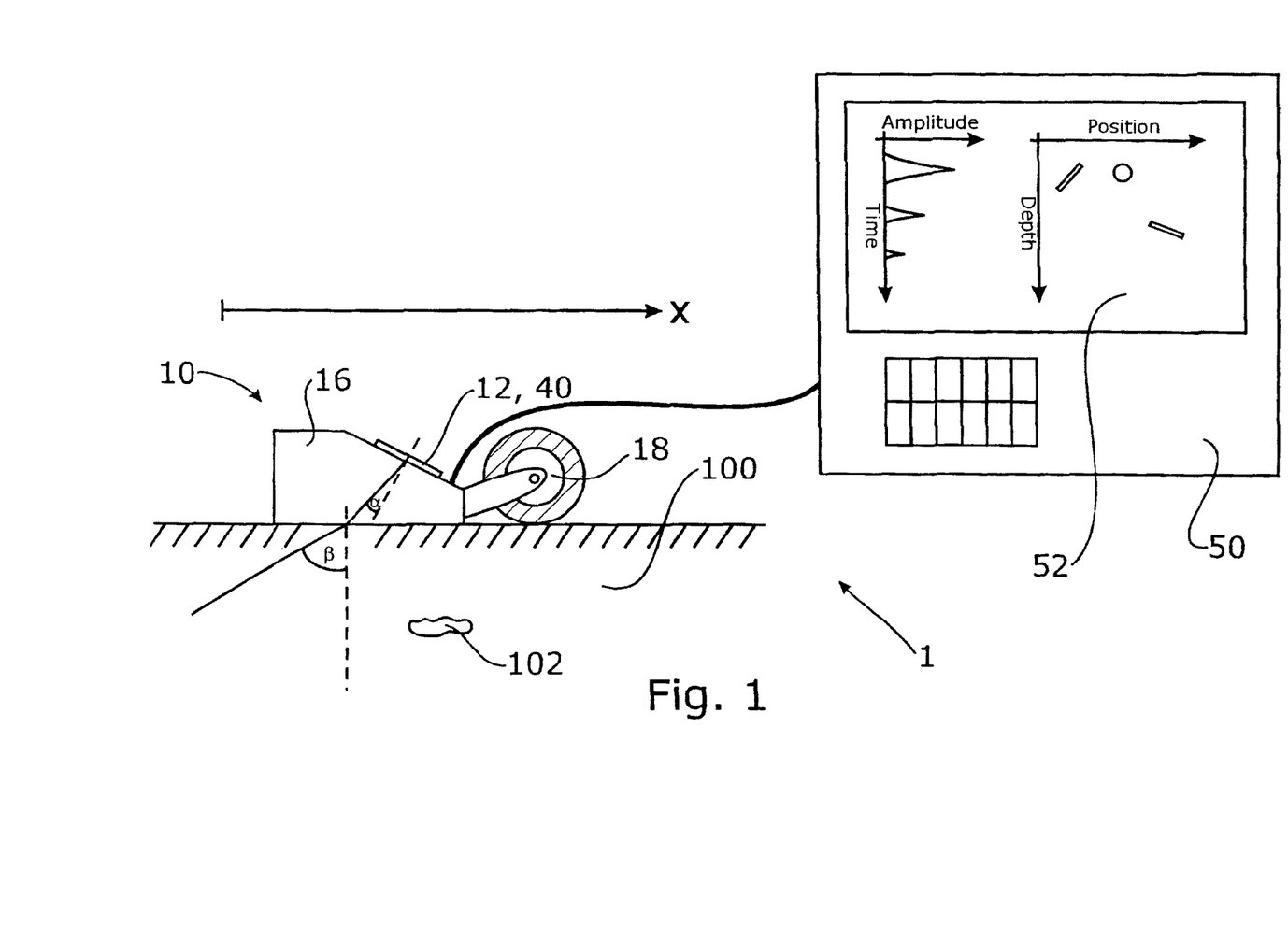
FIG. 1: shows schematic representation of a device according to the invention for the non-destructive testing of a test object.

FIG. 1 shows an exemplary embodiment of a device 1 according to the invention for the non-destructive testing of a test object 100 by means of ultrasound. The device 1 comprises a transmitting test probe 10, which in turn comprises a lead section 16 and an ultrasonic transmitter 12 disposed thereon. The ultrasonic transmitter 12 is in this case arranged on the lead section 16 such that when the ultrasonic transmitter 12 is excited to emit ultrasonic pulses, these are substantially coupled into the lead section 16. The lead section 16 can in this case be formed, for example, by a body of Plexiglass®, as is known in principle from the prior art. Preferably, the elements of the transmitting test probe 10 are combined in a single housing, which is not shown in the figure for reasons of clarity. The transmitting test probe 10 shown is an angle probe, which is provided to couple into the test object 100 the ultrasonic pulses emitted by the ultrasonic transmitter 12 at an angle of incidence $\beta$, which is measured against the surface normal of the incident surface of the test object 100. The use of angle probes is optional and not mandatory; depending on the case of application, test probes for a perpendicular insonification (i.e., $\beta=0°$) can also be used.

The ultrasonic transmitter 12 used in the transmitting test probe 10 is an ultrasonic transmitter of the phased array type, i.e., the ultrasonic transmitter 12 comprises a plurality of ultrasonic transducers 14, which form at least one linear arrangement and can be controlled individually. The longitudinal axis of the at least one linear array of the ultrasonic transducers 14 is in this case oriented in the direction marked X. By means of a specific adjustment of the phase position between the individual ultrasonic transducers 14, it is possible to dynamically influence the emission angle $\alpha$, i.e. the beam direction, within wide limits.

In the exemplary embodiment shown, the transmitting test probe 10 comprises a mechanical displacement sensor 18, which mechanically scans the movement of the transmitting test probe 10 on the surface of the test object 100 and provides corresponding position information, e.g., to a control unit 50 connected to the transmitting test probe 10. Alternatively, the displacement sensor 18 can also operate in a contactless manner, e.g., according to the principle of the optical mouse. The displacement sensor 18 is—regardless of its construction—preferably able to detect the movement of the transmitting test probe 10 in two directions independent of one another on the surface of the test object 100. Particular advantages result when rotary movements of the transmitting test probe 10 on the surface of the test object can also be detected. Based on the technology that is disclosed in the patent specification U.S. Pat. No. 7,324,910 B2, as well as the further development thereof which is disclosed in German patent application 10 2007 028 876.1 dated Jun. 26, 2007, a separately designed displacement sensor can be omitted completely, since the entire position information can be obtained from the signals of the ultrasonic transmitter 12 itself.

Connected to the transmitting test probe 10 is a control unit 50, which is configured to control the ultrasonic transducers 14 disposed in the ultrasonic transmitter 12 of the transmitting test probe 10 individually in a phase-accurate manner. Furthermore, the control unit 50 is configured to be connected to an ultrasonic receiver 40 in order to receive echo signals reflected back from a test object 10, which echo signals result from the ultrasonic pulses insonified from the ultrasonic transmitter 12. In the exemplary embodiment shown here, the ultrasonic transmitter 12 disposed in the transmitting test probe 10 also serves as an ultrasonic receiver 40. To this end, the separately formed and individually controllable ultrasonic transducers 14 contained in the ultrasonic transmitter 12 are electrically interconnected after the emission of a transmitted pulse to form a large-area ultrasonic transmitter 12, which then acts as the ultrasonic receiver 40. However, of course it is also possible to use a separately formed ultrasonic receiver 40, which can be arranged, e.g., in a separately formed receiving test probe. Such a separate receiving test probe would likewise comprise a lead section in the present exemplary embodiment, corresponding to the lead section 16 of the transmitting test probe 10.

For the non-destructive testing of a test object 100 for, for example, flaws 102 concealed in the volume of the test object 100, the transmitting test probe 10 is connected to the control unit 50 and placed on the surface of the test object 100. The acoustic coupling of the transmitting test probe 10 to the test object 100 is carried out as a rule using a suitable coupling means, which can be, for example, water, oil or also a water-based gel.

The test object 100 is preferably a mechanical workpiece or tool; however, it can also be a biological sample.

Now the tester moves the transmitting test probe 10 back and forth along the direction marked by X in FIG. 1 on the surface of the test object 100. At the same time he observes the display on a display device 52 associated with the control unit 50, which display device in the exemplary embodiment shown is integrated as a display into the control unit 50. An A-image is shown on the display device 52 in the exemplary embodiment shown, in which the amplitude of the ultrasonic pulses reflected back is shown for the given insonification location X as a function of the time. If the sound beam emitted by the transmitting test probe 10 strikes a flaw 102 in the volume of the test object 100, i.e., an ultrasound-reflecting structure such as a defect, a void or a crack, part of the insonified sound beam is reflected back and on the same route returns to the ultrasonic transmitter 12 of the transmitting test probe. As mentioned, this also acts at the same time as the ultrasonic receiver 40 which converts the sound signal reflected back into an electric signal, which is then outputted, optionally amplified in a suitable manner, to the control unit 50. In the control unit 50 the echo signal received, which is generally provided as an electrical signal, but which can also, if necessary, be transmitted by the transmitting test probe 10 in the form of an optical signal, is processed in a suitable manner; this can be carried out, for example, by highly time-resolved AD-conversion and signal processing. Subsequently, the signal is shown on the display device 52 in the form of the A-scan described above. If the insonified ultrasonic beam strikes a flaw 102, this results in echo signals that are directly visible in the A-scan. The approach described above is in this case advantageously carried out with a fixed insonification angle $\beta$.

Figure 2A:
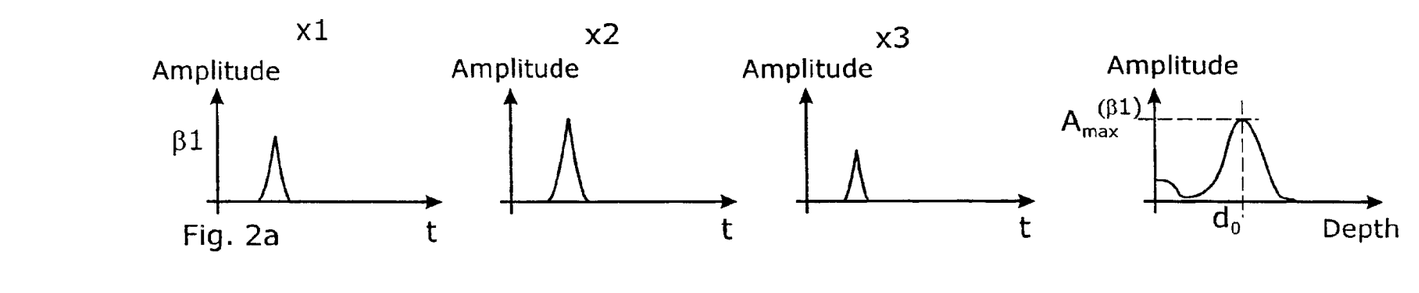
FIG. 2a-2c: shows an A-scan of the test object, recorded at different insonification positions x as well as at different insonification angles $\beta$, as well as the progression of the maximum amplitude Amax for a given insonification angle $\beta$ as a function of the depth d in the test object.

When the tester has discovered a flaw 102 with the procedure described above, he tries by variation of the X-position of the transmitting test probe 10 on the surface of the test object 100 to maximize the amplitude of the resulting flaw signal, i.e., to grow the signal. This growing of the signal is also carried out for a fixed insonification angle $\beta 1$. The A-scans resulting with the growing of the echo signal at various insonification locations X1, X2 and X3 are shown in FIG. 2a. It becomes clear that due to the change of the propagation path in the test object 100 the echo signal occurs at different times, but also varies in its maximum amplitude. This is due to the fact that, during the displacement of the transmitting test probe 10 on the surface of the test object 100, the center of the sonic cone in which the highest sonic pressure prevails is pushed over the flaw 102. As a rule, the maximum amplitude in the echo signal results when the sound beam strikes the flaw 102 centrally. If the envelope curve of all echo signals is determined for a fixed insonification angle $\beta 1$ with a variation of the insonification location X, a representation of the echo amplitude is obtained as a function of the propagation time or the depth of the flaw 102 in the test object 100, as is illustrated in the right-hand diagram of FIG. 2a. From this diagram the maximum echo amplitude Amax (β1) can be determined, which is the result for the selected insonification angle β1.

Thereafter the tester can vary the insonification angle β, so that he once again carries out the same investigation for a changed insonification angle β2. Alternatively, an automatic angle adjustment is also possible within the context of a (partially) automated test method. This also results in a diagram for the progression of the amplitude as a function of the time or of the depth of the flaw 102 in the test object 100. A diagram of this type is shown on the right in FIG. 2b. The maximum echo amplitude resulting in this case with the insonification angle β2 does not necessarily have to correspond to the echo amplitude with the insonification angle β1 selected first, as a rule there in this case will actually be a deviation, unless it is a regularly shaped flaw.

Figures 2B, 2C:
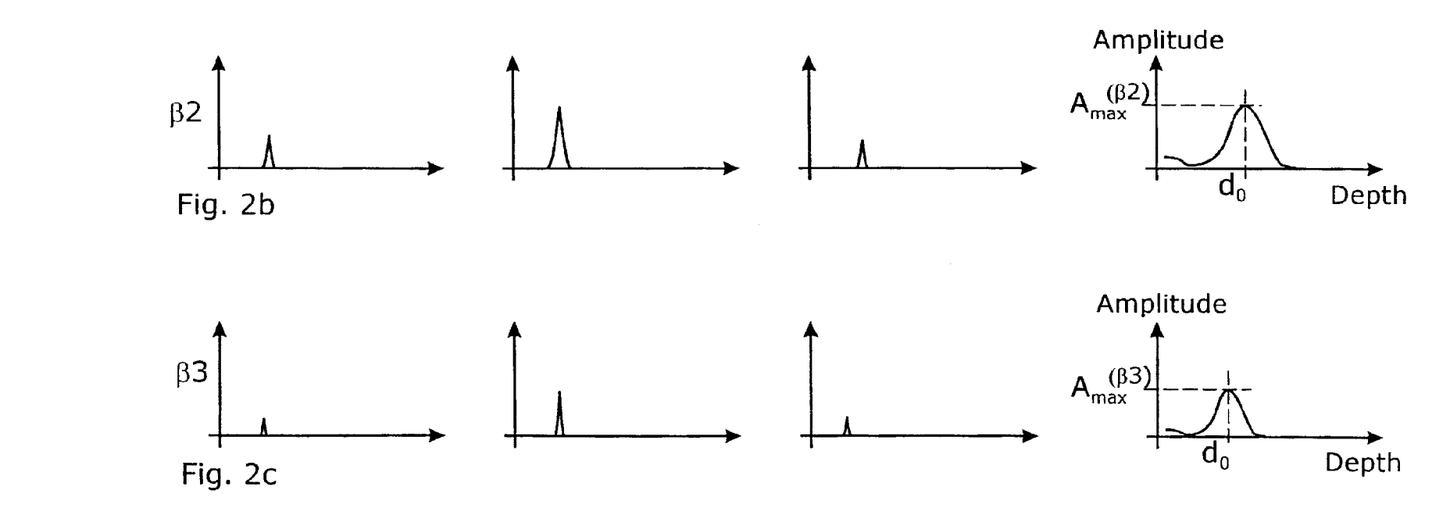

If the different propagation times that are the result of the different insonification angles β1 and β2 are compensated for, the peaks in the above-mentioned representation of the envelope curve Amax (β) lie substantially at the same point D0. However, if a propagation time compensation of this type is omitted, the peaks come to rest at different points.

The result of the same method for an insonification angle β3 changed once again is shown by way of example in FIG. 2c.

In the approach described above, the insonification angle β is electronically tuned utilizing the advantageous transmission properties of an ultrasonic transmitter 12 of the phased array type.

In an alternative embodiment, the control unit 50 is configured to automatically optimize a possibly resulting echo signal for a given insonification location X by variation of the insonification angle β.

Figure 3:
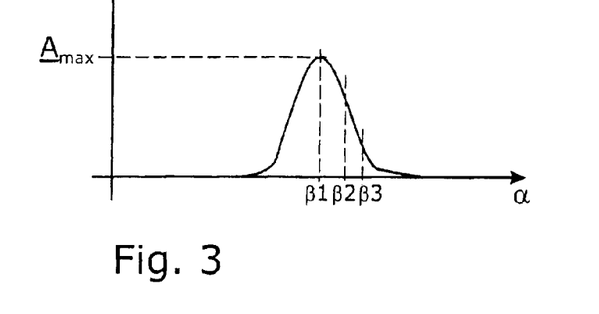
FIG. 3: shows a representation of the maximum echo amplitude Amax as a function of the insonification angle $\beta$.

If the maximum amplitudes Amax resulting for different insonification angles β are plotted over the corresponding insonification angle β, a diagram is obtained such as can be seen from FIG. 3. Now, the insonification angle β for which the examined flaw 102 shows the maximum echo amplitude Amax can be determined from this diagram or the underlying echo data. The angular dependence of the ultrasonic reflectivity of the flaw 102 can also be illustrated and analyzed from this in a simple manner. Possible interpretations of the behavior achieved with regard to the type of flaw 102 have already been described above.

Figure 4:
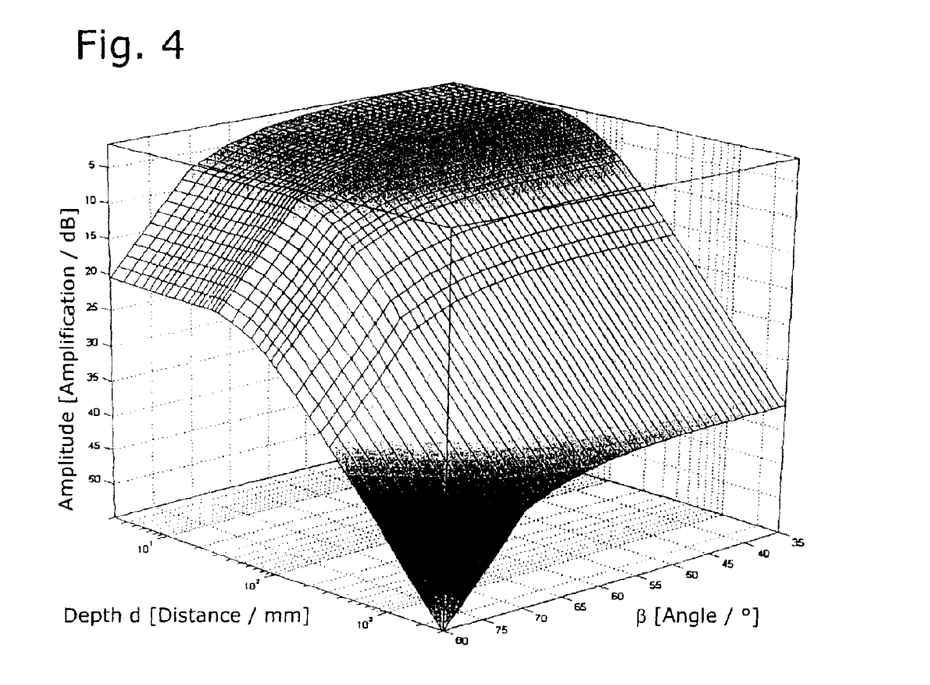
FIG. 4: shows an angle-resolved test probe-specific DGS diagram.

In the preparation for the practical testing of the test object explained above, so-called DGS diagrams are determined, as is known from the prior art for test probes with fixed insonification angle β. A DGS diagram in this case shows the echo amplitude of circular disk reflectors of different diameters and also of an extended flat reflector (back face echo) as a function of the distance, i.e. as a function of the depth d in the test object. In contrast to the DGS diagrams and devices for ultrasonic measurement previously known from the prior art, in which test probe-specific DGS diagrams are stored, for example, in digital form, the DGS diagrams are, within the context of the present invention, additionally recorded or generated in an angle-resolved manner and optionally stored in the control unit 50. FIG. 4 shows by way of example such a DGS diagram for a predetermined diameter of a circular disk reflector as a function of the distance d and as a function of the angle β.

To determine the ERS value of a flaw by means of a phased array test probe which permits an electronic variation of the insonification angle β into the test object 100, an adjustment of the general DGS diagram known from the prior art (cf. U.S. Pat. No. 5,511,425 A), which is based on theoretical considerations, can be necessary for various reasons. On the one hand, a calibration of the generally test probe-specific DGS diagram is necessary in order to take into account the ultrasonic properties of the material of the test object and to compensate for test probe-specific effects such as the aging of the ultrasonic transducer or a changed coupling of the transmitting test probe to the test object. To this end, before an actual test of a test object 100 is carried out, most test specifications conducting require a calibration step in order to calibrate the general DGS diagram, which can be already stored in the device 1.

Furthermore, it must be taken into account, in the case of an electronic variation of the insonification angle β by means of a phased array test probe, that the ultrasonic properties of the test probe themselves change directly because of the change of angle. For this reason, the general DGS diagram, which was determined for a specific insonification angle, must be converted for other (electronically adjusted) insonification angles β. In particular, it is possible to carry out this conversion in the device itself, so that a storage of a plurality of test probe-specific DGS diagrams for different insonification angles β is not necessary. In an alternative approach, it is of course also possible to store a plurality of, e.g., test probe-specific ones in the device 1 which relate to a plurality of insonification angles β. In this case the DGS diagrams can also be determined empirically or calculated theoretically.

Figure 5:
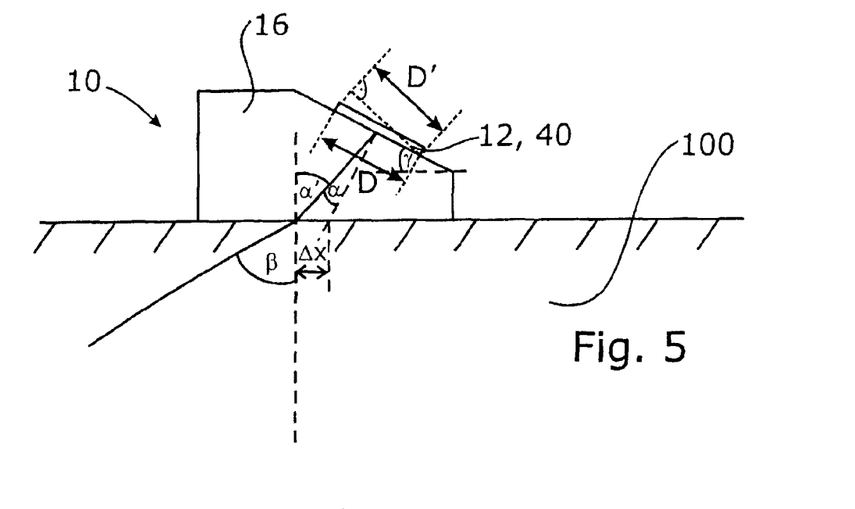
FIG. 5: shows a schematic representation of the beam geometry at the testing head.

As has already been explained above, the insonification angle β can be electronically tuned if a device according to the invention is used. As can be seen from FIG. 5, for example, in the case of an angle probe with a lead section, both the coupling-in point of the sound beam in the test object changes by AX, and the diameter of the sound beam changes with its transfer from the lead section into the test object when the insonification angle β is tuned electronically. This can also be interpreted as a virtual change of the dimensions of the ultrasonic transmitter 12 (D→D'), which likewise has to be taken into consideration in the recording of the DGS diagrams mentioned above. By means of simple geometric considerations and the law of acoustic refraction, it is possible to easily calculate the influence of the electronic change of the insonification angle β on the change of the coupling-in point and the size of the virtual ultrasonic transmitter (12).

In order now to determine an equivalent reflector size ERS for the flaw detected in the volume of the test object, the tester—as in the case of the devices already known from the prior art with test probes with fixed insonification angle β—has the DGS curve represented on the display device 52 of the control unit 50 that corresponds to the electronically adjusted insonification angle β at which the maximum echo signal Amax resulted. The DGS curve was in this case calibrated, prior to the actual measurement, on reference flaws which can be inserted in test objects, for example. The "calibration" is a calibration of the sensitivity of the test probe used. As a rule, the reference echo needed for this purpose is obtained from back face echoes on the standardized so-called "K1" or "K2" test pieces (depending on the frequency of the test probe used). Since in these cases, these are not flat back faces, a circular arc correction (generally specified by the manufacturer of the test probe) must also be carried out. Reference reflectors from the component, however, are rather rare.

The DGS curve displayed on the screen corresponds to a predetermined equivalent reflector size, which generally corresponds to the registration limit specified by the test specification. If a flaw is found, the echo of which exceeds the DGS curve shown on the screen, then, for example, the resulting equivalent reflector size ERS is indicated automatically by the control unit 50 (either in dB over the registration limit or directly in millimeters). In the DGS curve, plotting the propagation time of the pulse up to the detected flaw, the tester can therefore directly read off the equivalent reflector size ERS of the flaw.

In a largely automated test routine, the tester scans the surface of the test object 100 in the manner described above until he detects echo signals which in his opinion originate from a flaw 102 in the volume of the test object 100. If necessary, he manually carries out a certain optimization of the flaw signal in this case before he resets the control and evaluation unit 50 of the device 1 according to the invention to an automatic measurement mode. In this the control unit 50 controls the ultrasonic transmitter 12 such that the coupling-in point of the sound beam in the test object is displaced in the X direction on the surface of the test object 100. At the same time, the control unit 50 records the amplitude of the resulting flaw echo as a function of the coupling-in point and determines the maximum echo amplitude. The insonification angle β is kept constant in the process.

In a subsequent process step, the control unit 50 varies the insonification angle so that the flaw 102 to be measured in the volume of the test object 100 is insonified at a different angle β2. In this case, the control unit 50 also varies the coupling-in point of the emitted sound beam into the test object through suitable control of the ultrasonic transmitter 12, with the resulting echo amplitude being recorded at the same time. The maximum echo amplitude Amax (β2) at the adjusted insonification angle β2 is determined also in this case, i.e., the tester "grows" the echo signal.

By comparison with one or more test probe-specific and angle-specific DGS diagrams, the control unit 50 of the device according to the invention then automatically determines the ERS value of the measured flaw 102. To this end, the control unit 50 automatically compensates for the influence of the electronic variation of the emission angle α of the ultrasonic transmitter 12 on the coupling-in point of the ultrasonic beam into the test object and thus on the propagation time of the ultrasonic pulses from the ultrasonic transmitter 12 up to the flaw 102. Furthermore, the control unit 50 likewise automatically compensates for the influence of the electronic variation of the emission angle α of the ultrasonic transmitter 12 on the virtual transmitter size, as has been described above. The control unit 50 also automatically compensates for the change of position of the focus in the test object and for the changed propagation time in the leading body due to the changed sound path in the leading body. Finally, the control unit 50 automatically converts from the emission angle α to the insonification angle β, wherein optionally the material properties of the test object are taken into consideration.

As a result, an ERS value of the flaw 102 detected in the volume of the test object 100 as well as the insonification angle β at which the maximum flaw signal Amax results are obtained from the test method carried out manually as well as from the test method carried out automatically. These data can then be recorded.

Figure 6:
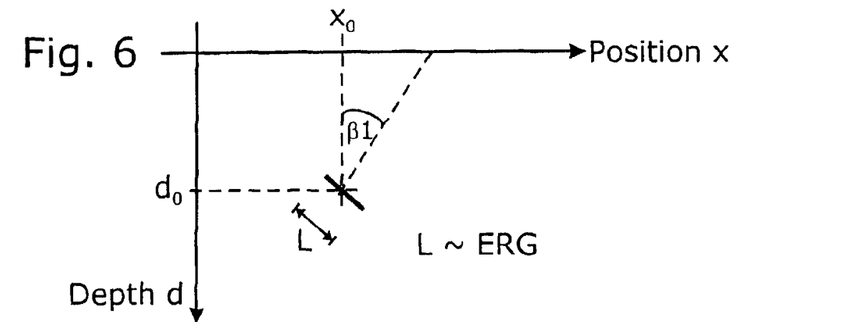
FIG. 6: shows an image representing a B-Scan of the test object, in which a flaw is represented by an associated ERS value.

If additional position information on the test probe is available, the test result can furthermore be illustrated in an easily accessible way in a B-scan, as is shown by way of example in FIG. 6, or also in a C-scan or S-scan. Thus a bar of the length L can be shown in the B-scan, the X-position of which on the surface of the test object corresponds to the position X0 at which the flaw is located by calculation. In the Y direction the bar is arranged at the depth D0, which corresponds to the calculated depth of the flaw in the volume of the test object 100. Furthermore, the length L of the bar that represents the measured flaw 102 is directly linked to the equivalent reflector size ERS of the flaw determined in the context of the test method according to the invention. Advantageously, the orientation of the bar is furthermore directly correlated with the insonification angle β at which the maximum echo signal Amax results. To this end, the longitudinal axis of the bar can be displayed tilted with respect to the X-axis such that the bar is oriented perpendicular to the sound propagation direction that corresponds to that insonification angle β at which the maximum echo signal results. The orientation of the bar in the B-scan shown in FIG. 6 provides the tester directly with information on the orientation of the measured flaw in the test object, which can also be recorded and stored. The B-scan shown schematically in FIG. 6 is in this case preferably also displayed to the tester on the display device 52, which is connected to the control device 50. Preferably, the control device 50 is configured to transmit the stored data to a PC where they can be subjected to a further evaluation.

Figure 7:
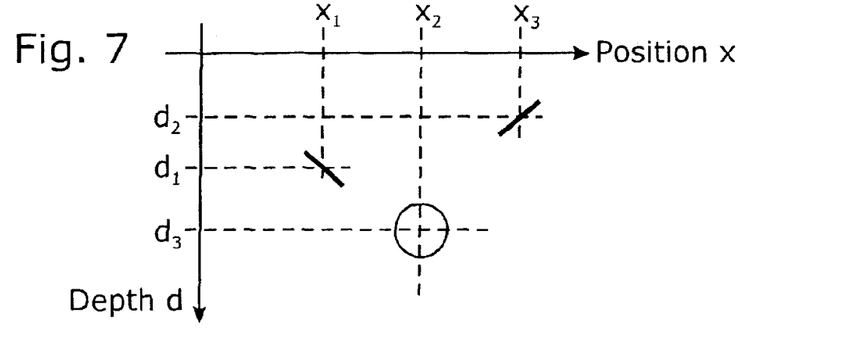
FIG. 7: shows a representation according to FIG. 6 of the test object with a plurality of flaws that have different reflection properties.

FIG. 7 finally shows another B-scan of a test object 100, from which three flaws 102 in the volume of the test object 100 can be seen. The flaws in this case lie at positions X1, X2 and X3. The flaws 102 detected at positions X1 and X3 in this case show a marked dependence of the echo signals on the insonification angle, i.e., the variation of the maximum flaw echo amplitude Amax resulting during a change of the insonification angle β exceeds a certain threshold value. It can be concluded from this that this is a flaw 102 of a more planar extension; accordingly, these flaws are shown in the B-scan of FIG. 7 as essentially one-dimensional symbols.

The flaw 102 detected at position X2, however, shows an echo amplitude essentially independent from the insonification angle β, i.e., the resulting variation of the echo amplitude remains below a predetermined threshold. A rather uniform three-dimensional extension of the flaw 102 can be concluded from this, which is shown in the B-scan of FIG. 7 by a two-dimensional flaw symbol (e.g., a circular disk as shown), the diameter of which is correlated with the equivalent reflector size ERS of this flaw.

Figure 8:
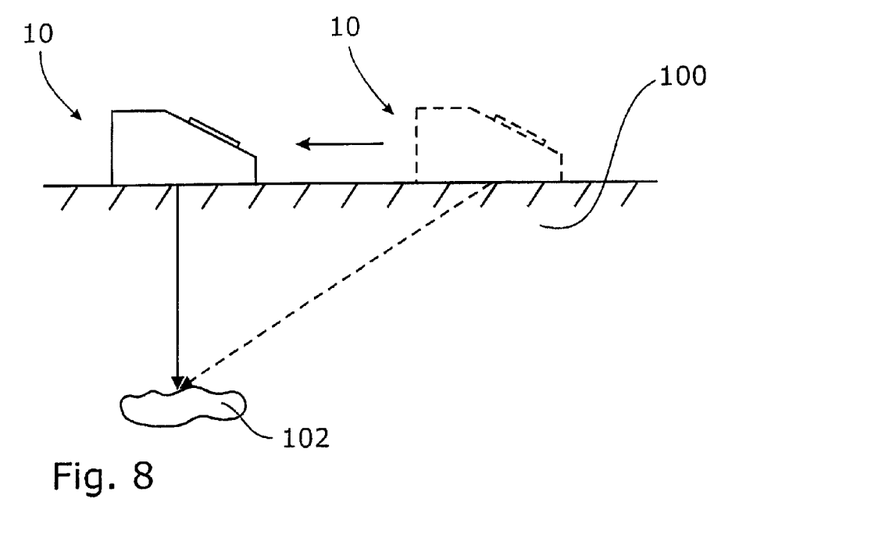
FIG. 8: shows a schematic representation of a method for detecting the angular dependence of the ERS value of a flaw in the volume of the test object.

A new method, which likewise is implemented in the device 1 according to the invention, is now illustrated on the basis of FIG. 8 *a*. In a first process step, the transmitting test probe 10 is controlled by the device 1 such that it insonifies ultrasonic pulses at a fixed angle of incidence β into the test object 100. When the tester has found a flaw 102 in the volume of the test object 100, he grows the flaw signal until the signal amplitude is at maximum. In a next step, he activates a "scan" function, in which the test probe 10 is controlled by the device 1 such that the insonification angle β into the test object 100 is electronically varied within a predetermined interval. The device 100 is furthermore configured to then determine from the flaw echoes received at the different insonification angles β the maximum flaw echo and the associated insonification angle β Max. If the position of the transmitting test probe 10 is changed on the surface of the test object 100, a changed insonification angle β results at which the flaw echo is maximal, since a maximum flaw echo is generally obtained when the flaw is acquired centrally by the ultrasonic beam. If, as described above, an electronic angle-scan is carried out, the device 1 can detect fully automatically the changed insonification angle β for which the flaw echo is at maximum. Via a variation of the position of the transmitting test probe 10 on the surface of the test object 100, the maximum flaw echo for different insonification angles β can be determined automatically by means of the method described above. In the process, the position of the transmitting test probe 10 on the surface of the test object 100 can on the one hand take place through a mechanical movement of the transmitting test probe 10, but it can also be varied virtually by carrying out a linear scan within the plurality of individual ultrasonic transducers 14 in the ultrasonic transmitter 12 (so-called "electronic linear scan").

If at least one DGS diagram, e.g., according to FIG. 4, is stored in the device, which, for example, can have been theoretically calculated or determined by means of practical measurements, then, from the maximum flaw echo amplitude determined for a certain insonification angle $\beta$, the ERS value of the flaw for this angle detected can be determined from the diagram. As the case may be, it can be necessary to calibrate the DGS diagram(s) stored in the device in a test probe-specific or material-specific manner based on a reference echo obtained on a test body, which reference echo optionally is recorded at different insonification angles, before the actual testing of the test object 100 is carried out. The DGS method thus permits in particular the automatic compensation for the sound paths resulting for the different insonification angles in the test object.

Alternatively, in the determination of the angle-dependent ERS-value of a flaw 102 in the volume of the test object 100, the device 1 can also utilize the position information that is supplied by the path detection unit 18. As described above, in a first step, for a fixed insonification angle $\beta$, the position of the transmitting test probe 10 on the surface of the test object 100 is sought for which the amplitude of the flaw echo is at maximum.

Subsequently a "trace" function on the device 1 is activated by the tester. When this is activated, the device 1 is configured to adjust, when the position of the transmitting test probe 10 changes, by means of suitable geometric calculations the insonification angle $\beta$ on the transmitting test probe 10 at which the flaw 102 in the test object is centrally acquired by the ultrasonic beam even with the changed transmitting test probe position. In the case of a displacement of the transmitting test probe 10 on the surface of the test object 100, the detected flaw 102 is then acquired centrally by means of the above-mentioned trace function at any time by the ultrasonic beam, so that the resulting flaw echo can be considered the maximum flaw echo for the set insonification angle $\beta$. The maximum flaw echo can thus be recorded as a function of the insonification angle $\beta$ directly by variation of the position of the transmitting test probe 10 on the surface of the test object 100 and the angle-dependent ERS value of the flaw 102 can be determined therefrom as a function of the angle $\beta$.

Figure 9A:
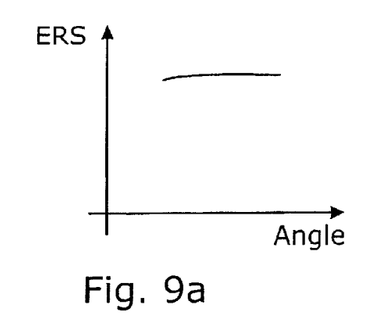
FIG. 9a, 9b: show schematic representations of the angle-dependent ERS value of two different flaws in the volume of the test object.
Figure 9B:
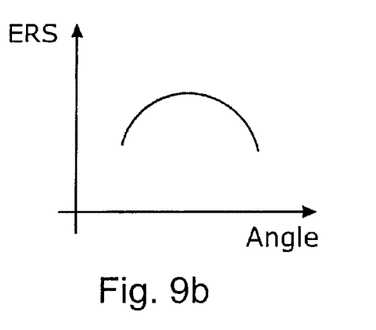

FIGS. 9a and 9b finally show by way of example the angle-dependent progression of the ERS value of two different flaws 102 in the volume of the test object 100. FIG. 9a in this case shows a flaw 102, the ERS value of which varies only slightly with the insonification angle P. This is therefore evidently a flaw 102, the ultrasonic reflection of which practically does not depend on the angle at which the flaw is struck by the ultrasonic beam. Consequently, it is to be assumed that the flaw is largely isotropic, at least with respect to that direction in space in which the position of the transmitting test probe 10 was varied during the above-mentioned examination.

FIG. 9b, however, shows a flaw whose ERS value depends very much on the insonification angle $\beta$. That means the ultrasonic reflectivity of the flaw 102 depends greatly on the angle at which the flaw 102 is detected by the ultrasonic beam. At least with respect to the direction in space in which the transmitting test probe was moved to detect the angular dependence of the ERS value, the flaw 102 to be classified is to be considered very anisotropic. It can thus be a crack, for example, which in all probability must be registered and therefore should be graphically marked in a suitable manner, for example, in a B-scan, C-scan or sector scan generated by the device 1, as has already been explained above.

The invention claimed is:

1. Method for the non-destructive testing of a test object by means of ultrasound, comprising the following steps:
    a. insonification of directed ultrasonic pulses into the test object at an insonification angle $\beta$, wherein the insonification angle $\beta$ is adjusted electronically,
    b. recording of the echo signals that result from the ultrasonic pulses insonified into the test object,
    c. determining an insonification position at which echo signals can be recorded which can be allocated to a flaw in the volume of the test object,
    d. determining an insonification angle $\beta$max for which an equivalent reflector size (ERS) value of the flaw has a maximum value at the position X0,
    e. changing the insonification position on a surface of the test object, wherein the change of the insonification position is detected, and
    f. electronic tracing of the insonification angle $\beta$ during the change of the insonification position, such that the ultrasonic pulses insonified into the test object strike the flaw always at the same position.

2. Method according to claim 1, wherein a graphic representation of the maximum ERS value is generated as a function of the insonification angle $\beta$.

3. Method according to claim 1, wherein a B-scan, a C-scan or a sector scan of the test object is generated, wherein at least one ERS value of a flaw found in the test object volume is depicted.

4. Method according to claim 3, wherein the dependence of the ERS value of the flaw found in the volume of the test object on the insonification angle $\beta$ is depicted.

5. Method according to claim 1, wherein the influence of the electronic adjustment of the insonification angle $\beta$ on the ERS value of the flaw to be determined is automatically compensated.

6. Method according to claim 1, wherein
    a. for insonification of directed ultrasonic pulses, a transmitting test probe is used whose ultrasonic transmitter comprises a plurality of independently controllable ultrasonic transducers, and
    b. for the electronic adjustment of the insonification angle $\beta$, the plurality of ultrasonic transducers is controlled individually and phase-accurately in such a way that an emission angle $\alpha$ of the ultrasound transmitter is varied.

7. Method according to claim 1, wherein at least one distance gain sizing (DGS) diagram is used to determine the ERS value of the flaw from the echo signals.

8. Method according to claim 7, wherein the DGS diagram is specific to a source of the ultrasonic pulses.

9. Method according to claim 7, wherein the DGS diagram has a dependence on the insonification angle $\beta$.

10. Method according to claim 7, wherein the DGS diagram is independent of the insonification angle $\beta$ and the influence of the insonification angle $\beta$ on a registered echo amplitude is compensated by calculation.

11. Method according to claim 1, further including a calibration step carried out at least once in which an amplitude of an echo caused by a reference flaw is detected.

12. Method according to claim 11, wherein the reference flaw is a back face or a test bore of a test piece.

13. Method according to claim 11, wherein the calibration step is carried out for a plurality of insonification angles $\beta$.

14. Method according to claim 4, wherein at least one of the following characteristics of the flaw is shown in a graphic representation of the flaw produced:
   a. insonification angle β at which the ERS value of the flaw is at maximum,
   b. information on whether the ERS value of the flaw is substantially constant over different insonification angle β.

15. Method according to claim 14, wherein
   a. the flaw is shown as a bar in the representation produced, and
   b. at least one of the following display parameters is used for coding the flaw characteristics to be shown:
      i. color,
      ii. angle of the longitudinal axis of the bar relative to the surface of the test object,
      iii. geometric basic form of the bar.

16. Device for the non-destructive testing of a test object by means of ultrasound, comprising
   a. a transmitting test probe with an ultrasonic transmitter, which is configured to insonify directed ultrasonic pulses at an insonification angle β into the test object,
   b. an ultrasonic receiver, which is configured to record echo signals of the ultrasonic pulses insonified into the test object,
   c. a control and evaluation unit, which is configured
      i. to control the ultrasonic transmitter of the transmitting test probe such that the ultrasonic transmitter is excited to emit ultrasonic pulses,
      ii. to process the echo signals recorded by the ultrasonic receiver, and
      iii. to determine an equivalent reflector size (ERS) value of the flaw from echo signals that can be assigned to a flaw in the volume of the test object,
   wherein
   d. the ultrasonic transmitter has a plurality of ultrasonic transducers that can be controlled independently, and
   e. the control and evaluation unit is configured:
      i. to control the plurality of ultrasonic transducers individually exactly in phase such that an emission angle α of the ultrasonic transmitter and thus, the insonification angle β into the test object, can be adjusted electronically,
      ii. to determine an insonification position at which the echo signals can be recorded which can be allocated to a flaw in the volume of the test object,
      iii. to determine an insonification angle βmax for which the ERS value of the flaw has a maximum value at the position,
      iv. in the case of a change of the insonification position on a surface of the test object,
         1. to detect the change of the insonification position, and
         2. to electronically trace the insonification angle β during the change of the insonification position such that the ultrasonic pulses insonified into the test object strike the flaw always at the same position.

17. Device according to claim 16, wherein the device is furthermore configured to generate a graphic representation of the maximum ERS value as a function of the insonification angle β.

18. Device according to claim 16, wherein the device is further configured to generate a B-scan, a C-scan or a sector of the test object, wherein at least one ERS value of the flaw found in the test object volume is depicted.

19. Device according to claim 18, wherein the device is further configured to depict the dependence of the ERS value of the flaw found in the volume of the test object on the insonification angle β.

20. Device according to claim 16, wherein the device is further configured to automatically compensate for the influence of the electronic adjustment of the insonification angle β on the ERS value of the flaw to be determined.

21. Device according to claim 17, wherein the generated graphic representation of the flaw is a B-scan, a C-scan or a sector scan.

22. Device according to claim 16, wherein the control and evaluation unit is configured to automatically compensate, during the calculation of the ERS value of the flaw, for the influence of the electronic adjustment of the insonification angle β on the ERS value of the flaw to be determined.

23. Device according to claim 16, wherein the device further comprises a path detection unit, which is configured to detect a change in the position of the test probe on the surface of the test object.

24. Device according to claim 18, wherein the detected flaw is symbolized by a bar in the generated scan, the extension of which along a longitudinal axis of the bar correlates with the ERS value of the detected flaw.

25. Device according to claim 18, wherein at least one of the following further characteristics of the flaw is depicted in the generated scan:
   a. relative amplitude of the flaw echo,
   b. insonification angle β at which the ERS value of the flaw is at maximum,
   c. relative flaw size,
   d. leg from which the flaw echo originates, and
   e. information on whether the ERS value of the flaw is substantially constant over different insonification angles β.

26. Device according to claim 25, wherein at least one of the following display parameters is used for coding the further flaw characteristics to be shown:
   a. color,
   b. dimension of the bar transverse to a longitudinal axis of the bar,
   c. angle of the longitudinal axis of the bar relative to the surface of the test object,
   d. geometric basic form of the bar.

27. Method according to claim 1, wherein the ERS value of the flaw at the changed insonification position is maximized by varying the insonification angle β.

28. Device according to claim 16, wherein the control and evaluation unit is furthermore configured to maximize the ERS value of the flaw at the changed insonification position by varying the insonification angle β.

* * * * *